US007663018B2

(12) United States Patent
Sommer et al.

(10) Patent No.: US 7,663,018 B2
(45) Date of Patent: Feb. 16, 2010

(54) TAU HYPERPHOSPHORYLATION IN TRANSGENIC MICE EXPRESSING THE APP DOUBLE MUTATION

(75) Inventors: Bernd Sommer, Eimeldingen (DE); Matthias Stauffenbiel, Lörrach-Haagen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/413,873

(22) Filed: Apr. 28, 2006

(65) Prior Publication Data

US 2007/0022483 A1    Jan. 25, 2007

Related U.S. Application Data

(63) Continuation of application No. 10/335,810, filed on Jan. 2, 2003, now abandoned, which is a continuation of application No. 09/841,971, filed on Apr. 25, 2001, now abandoned, which is a continuation of application No. 09/230,308, filed as application No. PCT/EP97/03991 on Jul. 23, 1997, now abandoned.

(30) Foreign Application Priority Data

| Jul. 19, 1996 | (GB) | ................................. 9615569.2 |
| Jun. 19, 1997 | (GB) | ................................. 9711262.7 |

(51) Int. Cl.
*A01K 67/00* (2006.01)
*A01K 67/033* (2006.01)
*A01K 67/027* (2006.01)
*G01N 33/00* (2006.01)
*C12N 15/00* (2006.01)
*C12N 5/00* (2006.01)

(52) U.S. Cl. ............................. 800/12; 800/18; 800/25; 800/3; 435/354; 435/29

(58) Field of Classification Search .................... 800/3, 800/12, 13, 18; 435/354
See application file for complete search history.

(56) References Cited

U.S. PATENT DOCUMENTS 5,877,399 A    3/1999 Hsiao

FOREIGN PATENT DOCUMENTS

| WO | 93/14200 | 7/1993 |
| WO | 94/12627 | 6/1994 |
| WO | 95/11968 | 5/1995 |
| WO | 96/06927 | 3/1996 |
| WO | 98/03644 | 1/1998 |

OTHER PUBLICATIONS

Andrä K. et al., Neurobiology of Aging, vol. 17 (2), "Expression of APP in Transgenic Mice: A Comparison of Neuron-Specific Promotors," pp. 183-190 (1996).

Chartier-Harlin, M-C et al., Nature, vol. 353, "Early-onset Alzheimer's disease caused by mutations at codon 717 of the β-amyloid precursor protein gene," pp. 844-846 (1991).
Games D. et al., Nature, vol. 373, "Alzheimer-type neuropathology in transgenic mice overexpressing V717F β-amyloid precursor protein," pp. 523-527 (1995).
P M Moran et al, PNAS Age related deficits in transgenic mice expressing the 751-amino acid isoform of human B-amyloid precursor protein, Jun. 1995, pp. 5341-5345.
KM Felsenstein, Alzheimer's and Parkinson's Diseases, Transgenic Rat and In-vitro Studies of B-amyloid precursor protein Processing, Plenum Press, NY, 1995, pp. 401-409.
L Lannfelt et al, Behaviorial Brian Research, Alzheimer's Disease: molecular genetics and transgenic animal models, 1993, 57, pp. 207-213.
LSHiggins, Annals NYAcedemy of Sciences, "Transgenic mice Expressing Human B-APP751, But not Mice Expressing B-APP695, Display Early Alzheimer's Diosease-like Histopathology", pp. 224-227.
Kaesermann H., Psychopharmacology, vol. 89, "Stretched attend posture, a non-social form of ambivalence, is sensitive to a conflict-reducing drug action*," pp. 31-37 (1986).
Kang J. et al., Nature, vol. 325, "The precursor of Alzheimer's disease amyloid A4 protein resembles a cell-surface receptor," pp. 733-736 (1987).
Kitaguchi N., Nature, vol. 331, "Novel precursor of Alzheimer's disease amyloid protein shows protease inhibitory activity," pp. 530-532 (1988).
Levy E. et al., Science, vol. 248, "Mutation of the Alzhelmer's Disease Amyloid Gene: Hereditary Cerebral Hemorrhage, Dutch Type," p. 1124-1126 (1990).
Mega M. et al., Neurology, vol. 46, "The spectrum of behavioral changes in Alzheimer's disease," pp. 130-135 (1996).
Moechars D. et al, EMBO Journal, vol. 15 (6), "Expression in brain of amyloid precursor protein mutated in the α-secretase site causes disturbed behavior, neuronal degeneration and premature death in transgenic mice," pp. 1265-1274 (1996).
Morris R.G.M. et al., Nature, vol. 297, "Place navigation impaired in rats with hippocampal lesions," pp. 681-683 (1982).
Quon D. et al., Nature, vol. 352, "Formation of β-amyloid protein deposits in brains of transgenic mice," pp. 239-241 (1991).
Schmidt E.V. et al., Molecular and Cellular Biology, vol. 10, "The Cytomegalovirus Enhancer: a Pan-Active Control Element in Transgenic Mice," pp. 4406-4411 (1990).
Sommer B. et al., Society for Neuroscience Abstracts 22:25 XP002049073, "Animal Models for Alzheimer's Disease Based on Genetics and Pathology," (Nov. 16, 1996).
Thiel G. et al., Proc. Natl. Acad. Sci. USA, vol. 88, "Characterization of tissue-specific transcription by the human synapsin I gene promoter," pp. 3431-3435 (1991).
Vidal M. et al., EMBO Journal, vol. 9 (3), "Tissue-specific control elements of the Thy-1 gene," pp. 833-840 (1990).
Wirak D.O. et al., Science, vol. 253, "Deposits of Amyloid β Protein in the Central Nervous System of Transgenic Mice," pp. 323-325 (1991).
Yankner B. et al., Science, vol. 245, "Neurotoxicity of a Fragment of the Amyloid Precursor Associated with Alzheimer's Disease," pp. 417-420 (1989).
Hsiao et al., Science, vol. 274, pp. 99-102 (1996).

*Primary Examiner*—Deborah Crouch

(57) ABSTRACT

Animal model involving transgenic manipulation of amyloid precursor protein, useful for testing potential therapeutic agents for the treatment of neurodegenerative disorders, in particular Alzheimer's disease.

15 Claims, 1 Drawing Sheet

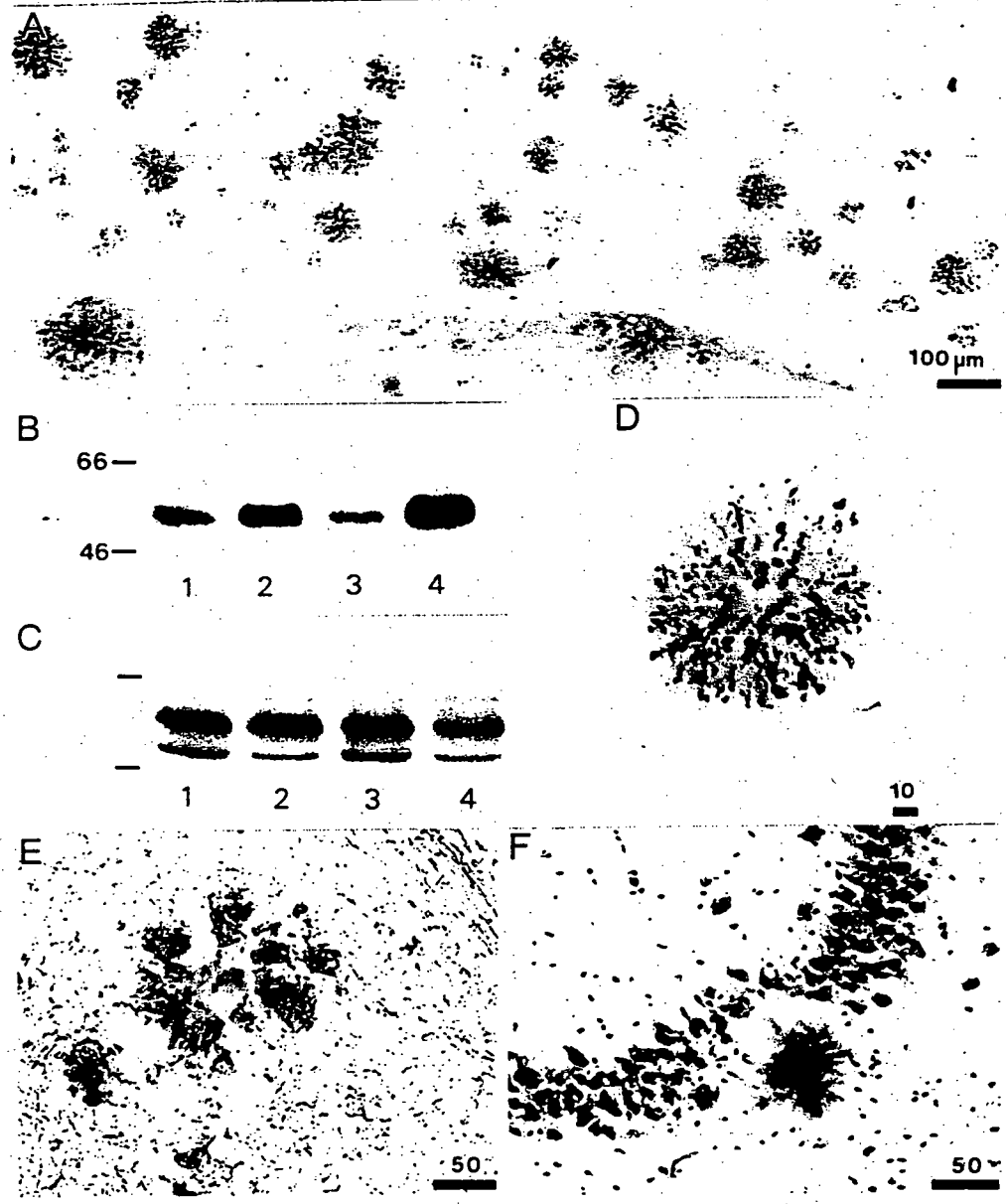

SEQUENCE LISTING (1) GENERAL INFORMATION:

(iii) NUMBER OF SEQUENCES: 1

(2) INFORMATION FOR SEQ ID NO: 1:

```
        (i) SEQUENCE CHARACTERISTICS:
            (A) LENGTH: 10 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO: 1:

GCCGCCATGG                                                              10
```

TAU HYPERPHOSPHORYLATION IN TRANSGENIC MICE EXPRESSING THE APP DOUBLE MUTATION

This is a continuation of application Ser. No. 10/335,810, filed on Jan. 2, 2003, which is a continuation of application Ser. No. 09/841,971, filed on Apr. 25, 2001 now abandoned, which is a continuation of application Ser. No. 09/230,308, filed on Jan. 22, 1999 now abandoned, which is a 371 of Application No. PCT/EP97/03992, filed on Jul. 23, 1997, the entire disclosures of which are hereby incorporated by reference.

The present invention relates to an animal model useful for testing potential therapeutic agents for the treatment of neurodegenerative disorders, in particular Alzheimer's disease (AD).

More particularly the invention relates to an animal model involving transgenic manipulation of amyloid precursor protein (APP).

The lack of an experimental animal model for AD that reflects the pathological mechanisms is a major obstacle for both basic research and drug development. As one approach to such models, reproduction of characteristic lesions such as senile plaques, neurofibrillary pathology, and cell loss in certain areas of hippocampus and cortex can be attempted. However, it is presently unclear whether these lesions are cause or consequence of the disease process. An alternative approach for model generation is to use factors known to lead to the disease. Recently, genetic studies revealed mutations in APP, which cosegregate with early onset of familial AD in the fifth or sixth decade of life and follow an autosomal dominant inheritance pattern. Three distinct missense mutations affect codon 717 of APP (altering V717→I {hereinafter referred to as the London mutation}, V717→G and V717→F in the polypeptide), while codons 670/671 (altering K670→N and M671→L in the polypeptide, hereinafter referred to as the Swedish mutation) are altered in the APP gene of a Swedish AD pedigree (numbers according to APP770). These mutations flank the part of APP that gives rise to βA4, the principal component of the filaments deposited in plaques in the brains of AD patients. In vitro studies have indicated that the Swedish mutation leads to increased formation of a soluble form of βA4, while the APP717 mutations gives rise to a higher proportion of a longer βA4 variant which facilitates filament formation. Together with the finding that filamentous βA4 is toxic in vitro, this suggests that the APP mutations may lead to AD via a mechanism involving βA4, but other mechanisms cannot be excluded.

More recently, transgenic mice have been generated, expressing APP with mutations in codons 717 and 670/671, using several neuron-specific promotors to drive expression of human APP cDNAs. Although protein levels reaching or exceeding the amount of endogenous APP have been obtained, the full pattern of histological alterations characteristic of AD have not been seen in the transgenic mice.

It has now surprisingly been found that by appropriate selection of APP expression construct, high levels of transgene mRNA are obtained, which exceed the endogenous APP message by up to 10 fold, and result in correspondingly elevated protein levels. Moreover, on histological analysis, significant deposits of human βA4 peptide are observed. Additionally and even more importantly, hyperphosphorylation of the microtubule-associated protein tau is achieved, which is a pathological phenotype associated to AD. Furthermore, the deposits accumulate cholinesterase staining associated with a local distorsion of cholinergic fibers typically observed in AD. Both features have not been reported previously with analogous transgenic animals. The pathology is accompanied with selective neuron loss in distinct areas of the brain.

Accordingly in a first aspect the invention provides a recombinant DNA construct comprising a polynucleotide encoding a human APP polypeptide comprising the Swedish mutation, functionally linked to a Thy-1 promoter element, provided that the Thy-1 promoter element is a rodent, e.g. mouse, Thy-1 promoter element when the Swedish mutation is the only mutation present in the APP polypeptide.

BRIEF DESCRIPTION OF THE DRAWING

FIG. 1 depicts Tau hyperphosphorylation, cholinesterase staining, and neuron loss in APP transgenic mice according to the invention. Staining of plaques with tau antibody AT8 recognizing phosphorylated Ser202 and Thr205 of tau is shown on a sagital free floating section of a transgenic mouse brain in FIG. 1A, and in higher magnification in FIG. 1D. Western blots of brain extracts from transgenic mice, 6 months (2) and 15 months (4) of age and littermate controls (1,3) are shown in FIGS. 1B and 1C. Blots were stained with antibodies AT8 (B) and N-tau7 (C) recognizing tau in a phosphorylation dependent and independent manner, respectively. Numbers indicate molecular weights of marker proteins in kDa. FIG. 1E shows staining for acetylcholine esterase in transgenic mice. A local distorsion of cholinergic fibers in the plaque vicinity can be noted. The loss of pyramidal neurons in the vicinity of Aβ deposits in area CA3 is shown in FIG. 1F by toluidine blue staining.

DETAILED DESCRIPTION OF THE INVENTION

Transgenic mice expressing said mutated human APP under control of said promotor have been found to develop a pathological phenotype which goes beyond that previously described by Games et al. [Nature 373, 523-527 (1995)], by combining APP and tau linked features of the AD pathology. Moreover, the mice have been found to present behavioural changes characteristic of AD, which has also never been reported before with transgenic animals.

It will be appreciated that such mice, by closely reflecting the AD pathology, as well as their transgenic cells, are particularly useful models of the disease.

Accordingly in a further aspect the invention provides transgenic non-human animals which exhibit both APP and tau-linked features, e.g. histological features, of AD pathology, and preferably also behavioural changes characteristic of AD.

Suitably the transgenic non-human animals express a human APP comprising the Swedish mutation or the Swedish mutation in combination with one or more additional mutations, in particular the London mutation. Suitably also the transgenic animal exhibits the features of AD pathology before 12 months of age preferably by about 6 months of age. Conveniently the transgenic animal is a rodent e.g. a mouse or a rat, preferably a mouse. This aspect of the invention includes transgenic cells derived from the transgenic non-human animal.

Without prejudice to the generality of the present invention, it appears that the level at which the transgene is expressed in the transgenic animal e.g. the level of transgene mRNA, is an important factor for obtaining AD pathology in the animal.

Thus in a further aspect the present invention provides a transgenic non-human animal cell, wherein DNA coding for a human APP having only one mutation is expressed at such a level that the amount of transgene mRNA exceeds the endogenous APP message by about 5 times, e.g. from 3 to 6 times, or more, e.g. from about 5 to about 10 times, as well as a transgenic non-human animal, e.g. a mouse or a rat, preferably a mouse, in the cells of which DNA coding for a human APP having only one mutation is expressed at such a level that the amount of transgene mRNA exceeds the endogenous message by about 5 times or more.

The only one mutation present in the APP polypeptide may comprise any APP mutation, including the Swedish mutation or the London mutation or other mutations at amino acid 717. Preferably the only one mutation is the Swedish mutation.

It furthermore appears that the number of genetic lesions influencing the production of βA4 introduced in a transgenic animal is another important factor for obtaining AD pathology in the animal.

The invention also provides a transgenic non-human animal cell, wherein DNA coding for a human APP having 2 mutations is expressed at such a level that the amount of transgene mRNA exceeds the endogenous APP message by about 2 times, e.g. from 1.5 to 3 times, as well as a transgenic non-human animal, e.g. a mouse or a rat, preferably a mouse, in the cells of which DNA coding for a human APP is expressed at such a level that the amount of transgene mRNA exceeds the endogenous message by about 2 times.

Further the invention provides a transgenic non-human animal cell, wherein DNA coding for a human APP having 3 or more mutations is expressed at such a level that the amount of transgene mRNA exceeds the endogenous APP message by less than 2 times, e.g. from about 1 to 2 times, as well as a. transgenic non-human animal, e.g. a mouse or a rat, preferably a mouse, in the cells of which DNA coding for a human APP is expressed at such a level that the amount of transgene mRNA exceeds the endogenous message by less than 2 times.

The 2 mutations or 3 or more mutations may comprise any combination of 2 or 3 or more APP mutations. Preferably, however, such multiple mutations comprise a combination of the Swedish and London mutations.

The DNA coding for human APP may comprise cDNA and/or genomic DNA, and is conveniently cDNA.

More particularly the present invention provides a transgenic non-human animal cell, wherein DNA encoding a human APP polypeptide comprising the Swedish mutation is expressed under the transcriptional control of a Thy-1 promotor element, as well as a transgenic non-human animal, e.g. a mouse or a rat, preferably a mouse, in the cells of which DNA encoding a human APP polypeptide comprising the Swedish mutation is expressed under the transcriptional control of a Thy-1 promotor element, provided that when the Swedish mutation is the only mutation present in the APP polypeptide the Thy-1 promoter element is a rodent, e.g. mouse, Thy-1 promoter element.

Transgenic animals according to the invention include animals into which the construct has been introduced directly as well as progeny of such animals which retain the ability to express the construct.

Cells manipulated according to the invention may be prepared by any known transfection technique. The DNA sequence may be introduced by direct genetic manipulation or into an earlier generation of the cell. Thus, the cells may be obtained from transgenic animals and cultured in vitro.

Also the transgenic animals may be generated according to well established methods, such as manipulation of embryos, e.g. by gene transfer into embryonic stein cells, retroviral infection of early embryos or pronuclear microinjection.

The pronuclear microinjection technique is preferred. Transcription units obtained from a recombinant DNA construct of the invention are injected into pronuclei of animal embryos and the obtained founder transgenics are bred.

The results obtained in the offspring can be analysed using various techniques well known in the art. Thus, for example, transgene APP mRNA expression is analysed by RNA blotting, the expression pattern of the transgene in the brain is determined by in situ hybridization, detection of APP in the brain is effected using immunoblotting techniques (western blot analysis) and the effects of the expression are studied by histology and immunohistology.

Models based on cells and animals of the invention may be used for example to identify and assess the efficacy of potential therapeutic agents in neurodegenerative diseases, particularly in diseases where βA4 peptide is deposited and/or the microtubule-associated protein tau is hyperphosphorylated, more particularly in AD. In particular such models may be used in screening or characterization assays for detecting agents likely to prevent βA4 deposit and/or hyperphosphorylation of tau.

Accordingly in a further aspect the invention comprises a method for testing a potential therapeutic agent for a specified condition, in particular a neurodegenerative disease, preferably AD, wherein a cell of the invention is used as target cell. More particularly it comprises such a method, wherein the agent is administered to a transgenic non-human animal of the invention. Moreover the invention comprises a screening or characterization assay consisting in or including such a method, as well as a screening assay kit comprising cells of the invention.

Methods for screening potential therapeutic agents using cell lines or animals are well known in the art. The cells and animals of the present invention may be used in analogous manner.

The recombinant cells may for example be incubated with the potential therapeutic agent and with antibodies recognizing βA4 amyloid in typical senile and diffuse plaques and/or with tau antibodies staining neurofibrillary tangles in the Alzheimer brain. In methods where the transgenic animals themselves are used, the effects of the potential therapeutic agent may be determined by carrying out various investigations on the animals after sacrifice. Also after administration of the potential therapeutic agent, the transgenic animal may undergo behavioural testing in order to monitor cognitive function.

The techniques of detection of βA4 and protein tau, including Western blot analysis, and the antibodies used therefor, are also well documented.

Compounds for use in the treatment of neurodegenerative diseases, which have been identified using an assay or assay kit as defined above, are also part of the present invention.

The following example illustrates the invention:

Expression Construct

Human APP751 cDNA carrying the Swedish double mutation is modified at the 5' end to reconstitute an optimal translation initiation sequence (GCC GCC ATG G).

This cDNA starting at above sequence and extending to nucleotide 3026 (Hind III site) is inserted into the Xho I cloning site of a pUC18-based vector containing an 8.1 kb EcoRI fragment comprising the mouse Thy-1.2 gene [Vidal et al. (1990) EMBO J. 9, 833-840]. The vector is modified such that a 1.5 kb BanI-Xho1 fragment carrying exon 3 and flanking intervening sequences is replaced by a linker sequence encoding the unique Xho I recognition site [Moechars et al. (1996) EMBO J. 15, 1265-1274]. Transcription units are released by NotI/PvuI digestion.

Expression construct APP 14 described in K. Andrä et al., Neurobiology of Aging, Vol. 17, No. 2, 183-190 (1996) is modified by replacing a 600 bp Bgl II/Spe I fragment with a corresponding fragment of a human $APP_{751}$ cDNA carrying the London mutation V 717→I. Transcription units are released by Not I digestion.

Three promoter elements (rat neuron specific enolase, NSE; human rhombotin I and human Thy-1) were inserted into the vector pBSNOTSV40, which is derived from pBluescript and contains a HindIII/BamHI fragment with Simian virus 40 early polyadenylation and splice sites. The T-antigen coding sequence between the HpaI site at map position 2670 and map position 4487 (47) was deleted. An additional NotI restriction site is present at the position of the XhoI site of the pBluescript polylinker to facilitate the release of the inserted transcription unit. For the rhombotin expression vector a 8 kb XhoI/NruI fragment containing a rhombotin promoter element from human clone pA27 was cloned into the polylinker of pBSNOTSV40. To generate the Thy-1 expression plasmid, a 3.6 kb EcoRI fragment was inserted after an EcoRI site had been generated at the initiator codon of a 8.2 kb human Thy-1 genomic fragment. A 2.3 kb BglII/NcoI rat NSF promoter fragment was used to obtain the NSF expression vector. The NcoI site had been introduced immediately proximal to the start codon. The vector pGCHNFL contains promoter and regulatory elements of the human neurofilament L (NF-L) gene. The APP cDNAs inserted into all expression vectors encoded full-length human APP751 including the signal peptide. An APP cDNA fragment mutated at codon 717 [valine to isoleucine] was inserted downstream of the rhombotin promoter element. This fragment starts with the initiation codon [position 125] and extends to a HindIII site in the 3' untranslated region of APP (position 3026).

This construct was used to generate the mouse line APP2. The Thy-1 construct was used to generate the mouse line APP2. The Thy-1 (APP10), NSE (APP12), and NF-L (APP16) vectors contain the same cDNAs except that a GCC triplet was introduced immediately 5' of the ATG to enhance translation as described by Kozak and the fragment comprises additional 3' untranslated sequence (up to position 3147, EcoRI site). The mutations at amino acid position 670/671 (lysine/methionine to asparagines/leucine) were introduced by exchanging a BglII/EcoRI fragment of the APP cDNA with two complementary oligonucleotides GAT CTC TGA AGT GAA YCY GGA TGC AG, AAT TCT GCA TCC AGA TTC ACT TCA GA, which leave compatible overhangs. The optimal Kozak consensus sequence (GCC GCC ATG G) was introduced by PCR amplification. An APP cDNA starting at this sequence and extending to nucleotide 3026 (HindIII site) was inserted into the Thy-1 vector (APP14). Before injection the vector sequences were removed.

Generation of Transgenic Mice

Isolated transcription units are injected into the pronuclei of B6D2F1×B6D2F1 embryos to generate transgenic founder animals.

Northern Blot Analysis, In Situ Hybridization, Western Blot Analysis, Histology and Immunohistology are performed according to the methods described in K. Andrä et al., Neurobiology of Aging, Vol. 17, No. 2, 183-190 (1996).

Results

Offspring of the founder animals express human APP mRNA in high amounts throughout all brain structures as demonstrated by in situ hybridization. Determined amounts of transgene derived protein exceed those of endogenous APP 5 to 10 fold. At 6 months of age, these mice show extracellular deposits of human βA4 peptide in cerebral cortex and the hippocampal formation. These deposits are positive in methenamine silver impregnation, thioflavin S staining and in Congo Red birefringence. They are surrounded by reactive astrocytes and dystrophic neurites. In addition, plaques are immunoreactive with antisera specific to hyperphosphorylated microtubule associated protein tau as found in brains of AD patients, which has not been reported previously for analogous transgenic animals. Hence, the described deposits in the brains of these mice closely resemble senile plaques found in AD patients. When stained for acetylcholinesterase, a strong labelling of plaques and a local distorsion of the cholinergic fibre network is observed. Plaques contain acetylcholinesterase activity in structures resembling swollen, dystrophic neurites. This degeneration of cholinergic neurites is another well-known feature associated with AD. Furthermore, a local degeneration of neurons in the plaque vicinity is observed in areas typically affected in AD such as hippocampal CA1. Here, the neuron loss is negatively correlated to the plaque burden and can reach up to 20%.

Tau hyperphosphorylation, cholinesterase staining and neuron loss in APP transgenic mice according to the invention are illustrated in FIG. 1. Staining of plaques with tau antibody AT8 recognizing phosphorylated Ser202 and Thr205 of tau is shown on a sagital free floating section of a transgenic mouse brain in A and in higher magnification in D. Western blots of brain extracts from transgenic mice, 6 months (2) and 15 months (4) of age and littermate controls (1,3) are shown in B and C. Blots were stained with antibodies AT8 (B) and N-tau7 (C) recognizing tau in a phosphorylation dependent and independent manner, respectively. Numbers indicate molecular weights of marker proteins in kDa. E shows staining for acetylcholine esterase in transgenic mice. A local distorsion of cholinergic fibers in the plaque vicinity can be noted. The loss of pyramidal neurons in the vicinity of Aβ deposits in area CA3 is shown in F by toluidine blue staining.

Behavioural Testing

Transgenic mice obtained as described above show significant non-cognitive behavioural changes corresponding to changes observed with patients suffering from AD, as reported by Mega et al. (1996) Neurology 46, 130-135.

For example in the Half-Enclosed Platform test according to a modification of Käsermann (1986) Psychopharmacol. 89, 31-37, compared to non-transgenic littermates, the animals avoided the open half and an increase of exploratory-behavioural moves and postures such as locomotion and head raising, indicative of agitation, disinhibition and irritability as reported for AD patients was observed.

Cognitive Testing

Furthermore the mice show significant cognitive impairment.

For example in the water maze according to Morris et al. (1982) Nature 297, 681-683, compared to non-transgenic littermates, the animals made significantly less crossings of the annulus representing the platform's previous position (2.5±0.5 vs. 4.4±0.7; p<0.05, 2-tail Mann-Whitney U-test) and spent a significantly lower percentage of time in the quadrant containing the annulus (20.8±3.8 vs. 33.1±3.2; p<0.05, 2-tail Mann-Whitney U-test).

The invention claimed is:

1. A cell obtained from a transgenic mouse wherein the cell comprises integrated into its genome a transgene comprising a DNA sequence encoding a human APP polypeptide functionally linked to a rodent Thy-1 promoter element, wherein the human APP polypeptide comprises the Swedish double mutation.

2. The cell of claim 1 wherein the Swedish double mutation is modified at the 5' end to contain a translation sequence of GCC GCC ATG G.

3. A transgenic whose mouse genome comprises a transgene comprising a DNA sequence encoding a human APP polypeptide functionally linked to a rodent Thy-1 promoter element, wherein the human APP polypeptide comprises the Swedish double mutation and wherein human βA4 polypeptide is deposited in the brain of said mouse.

4. The transgenic mouse of claim 3 wherein the Swedish double mutation is modified at the 5' end to contain a translation sequence of GCC GCC ATG G.

5. The transgenic mouse of claim 3 wherein the amount of transgene mRNA exceeds the endogenous APP mRNA by two times or more.

6. The transgenic mouse of claim 3 wherein said deposits are extracellular.

7. The transgenic mouse of claim 3 wherein said mouse exhibits hyperphosphorylation of the microtubule associated protein tau.

8. A method for testing a potential therapeutic agent for treatment of a neurodegenerative disease, comprising
   i. contacting a transgenic whose mouse genome comprises a transgene comprising a DNA sequence encoding a human APP polypeptide functionally linked to a rodent Thy-1 promoter element, wherein the human APP polypeptide comprises the Swedish double mutation and wherein human βA4 polypeptide is deposited the brain of said mouse; and
   ii. assessing the effect of said agent on the deposition of Aβ4.

9. The method of claim 8, wherein the step of contacting comprising administering the agent to said mouse.

10. The method of claim 8, wherein the neurodegenerative disease is Alzheimer's disease.

11. The method of claim 8 further comprising the step of detecting Aβ4 deposition and, optionally detecting hyperphosphorylation of the microtubule associated protein tau.

12. A screening assay kit comprising cells according to claim 1.

13. A method for testing a potential therapeutic agent for treatment of a neurodegenerative disease, comprising
   i. contacting a brain cell isolated from a transgenic mouse, the cell comprises integrated into its genome a transgene comprising a DNA sequence encoding a human APP polypeptide functionally linked to a rodent Thy-1 promoter element, wherein the human APP polypeptide comprises the Swedish double mutation; and wherein the cell expresses human APP comprising a Swedish double mutation; and
   ii. assessing the effect of said agent on the production of Aβ4.

14. The method of claim 13, wherein the neurodegenerative disease is Alzheimer's disease.

15. The method of claim 13 further comprising the step of detecting Aβ4 deposition and, optionally detecting hyperphosphorylation of the microtubule associated protein tau.

* * * * *